United States Patent [19]

Kinanen

[11] Patent Number: 5,555,251
[45] Date of Patent: Sep. 10, 1996

[54] ARRANGEMENT TO MINIMIZE EDDY CURRENTS IN MR IMAGERS

[75] Inventor: Ilmari V. Kinanen, Espoo, Finland

[73] Assignee: Picker Nordstar Inc., Helsinki, Finland

[21] Appl. No.: 255,330

[22] Filed: Jun. 7, 1994

[30] Foreign Application Priority Data

Jun. 8, 1993 [FI] Finland ........................... 932615

[51] Int. Cl.⁶ ............................ G01V 3/00; G01V 3/14
[52] U.S. Cl. ..................... 324/319; 324/318; 324/322
[58] Field of Search ................................. 324/318, 319, 324/322

[56] References Cited

U.S. PATENT DOCUMENTS

| | | | |
|---|---|---|---|
| 4,818,966 | 4/1989 | Miyamoto et al. | 335/296 |
| 4,827,235 | 5/1989 | Inomata et al. | 335/297 |
| 4,870,380 | 9/1989 | McGinley | 335/296 |
| 5,124,651 | 6/1992 | Danby et al. | 324/318 |
| 5,194,810 | 3/1993 | Breneman et al. | 324/319 |
| 5,243,286 | 9/1993 | Rzedzian et al. | 324/318 |
| 5,414,399 | 5/1995 | Breneman et al. | |

FOREIGN PATENT DOCUMENTS

| | | |
|---|---|---|
| 0479514 | 4/1992 | European Pat. Off. |
| 2-87505 | 3/1990 | Japan . |
| 2-184002 | 7/1990 | Japan . |

OTHER PUBLICATIONS

Patent Abstracts of Japan: vol. 14, No. 278, p. 5 Published: Jun. 15, 1990 Author: Hideya Sakurai.
Patent Abstracts of Japan: vol. 14, No. 457, p. 51 Published: Oct. 2, 1990 Author: Hideya Sakurai.
Patent Abstracts of Japan: vol. 13, No. 326, p. 110, Jul. 24, 1989 Author: Kimio Matsumoto.

Primary Examiner—Sandra O'Shea
Assistant Examiner—Mack Haynes
Attorney, Agent, or Firm—T. B. Gurin; J. J. Fry

[57] ABSTRACT

Two opposite iron core pole pieces of a magnetic resonance medical imager generate a static magnetic field in a patient imaging volume disposed between the pole pieces. Gradient coils are positioned in the face of a pole piece. Thin disc shaped (42, 44) or ring shaped (41) ferromagnetic parts laminated of layers cut favorably from transformer sheet material are attached to the face of the pole piece. Each layer is electrically insulated from adjacent layers and surfaces by enamel or fixing glue. To reduce eddy currents in these layers, narrow, radially oriented slots (43, 45) are cut in these layers before lamination. The slots are oriented in the adjacent layers so as not to coincide resulting in improved conduction of the magnetic flux in the imaging volume during the production of gradient magnetic fields by the gradient coils.

17 Claims, 6 Drawing Sheets

ARRANGEMENT TO MINIMIZE EDDY CURRENTS IN MR IMAGERS

BACKGROUND OF THE INVENTION

This invention relates to a pole piece design to greatly reduce the disadvantageous eddy current effects caused by the gradient pulses used in medical magnetic resonance imaging equipment or MRI equipment.

In MRI equipment there is a necessity to superimpose strong, rapidly changing gradient fields on very homogeneous static magnetic field. These gradient fields spatially define the imaging volume, and are produced by coils carrying precisely controlled current pulses. Due to the need for very rapid changes in the magnetic fields there will be eddy currents induced in all electrically conducting parts near to the gradient coils. These eddy currents tend to oppose the rapid increase of the field. In MRI magnets using pole pieces to produce strong homogeneous field this is a difficult problem which slows down the gradient ramps and causes eddy currents with various damping times in complex shaped pole pieces. The electric compensation of those is usually not totally successful, and moreover the eddy currents cause heating of the pole pieces. This has an adverse effect on the stability of the static magnetic field.

There have been efforts to solve the problem described above by using electrically non-conducting, sintered ferrite in the pole pieces. This is effective in relatively weak magnets only, because the permeability of the ferrite decreases in strong fields due to saturation. The U.S. Pat. No. 4,827,235 patent describes the reduction of the gradient rise time from three milliseconds to one millisecond by using a higher resistivity material instead of iron in the pole piece. The U.S. Pat. No. 5,124,651 patent describes a solution using insulated ferromagnetic pieces clamped tightly together in an assembly where the shortest dimension of these pieces is perpendicular to the symmetry axis of the pole piece. This arrangement, however, is very difficult to implement with the high mechanical precision needed in practice. Moreover the magnetic return flux of the gradient coils should have lowest possible reluctance, preferably using an isotropic path on the pole piece surface. Another embodiment of this patent describes the use of layers of thin sheets arranged perpendicular to each other. However, this doesn't meet the isotropicity requirement, as the outermost layer carries more of flux in the direction of the sheets than in the perpendicular direction, thus resulting in an asymmetric magnet design.

The pole piece suggested by U.S. Pat. No. 4,827,235 is made for example of either an expensive amorph mixture of metals or a composite mixture, which also is expensive and does not meet the demand of sufficiently high permeability. The pole piece of U.S. Pat. No. 5,124,651 is highly expensive to build, as there is a necessity to pack from thousands of pieces an entity of the right form with far better than millimeter accuracy and hold all the pieces stable in their places. In addition, in order to reach high homogeneity in the magnet the pole piece shape must be strongly profiled with concentrically arranged annular shapes in the pole piece face and cannot be a substantially flat surface, as proposed here.

The English abstract of Japanese Patent Application JP 2-184002 set forth in Patent Abstracts of Japan, Vol. 14, No. 457, pg 51, Oct. 2, 1990, describes an MRI magnet having a magnetic pole piece composed of a bulk member which consists of a disc-shaped magnetic substance having a projection at the center and a laminated part. The laminated part has a magnetic thin plate and an electrically insulating member laminated alternatively in a spiral shape on the plane of the bulk member around the projection. The laminate part is divided by a plurality of radial grooves arranged radially from the center of the projection.

The English abstract of Japanese Patent Application JP 2-87505 set forth in Patent Abstracts of Japan, Vol. 14, No. 278, pg 5, Jun. 15, 1990, describes an MRI magnet having a magnetic pole segment of a circular plate type formed of a central bulk part wherein the air-gap facing surface is constituted of a flat surface. The outer peripheral side thereof is formed of an outer peripheral part having a plurality of radial grooves arranged radially from the center of the bulk part. The surface of the outer peripheral part is divided by the grooves into a plurality of parts which face an inclination magnetic field coil. The inclination field coil generates eddy currents in the vicinity of the magnetic pole segment.

In the configurations set forth in the above two Japanese Patent Applications eddy currents can penetrate into the bulk portion of outer peripheral part of the pole face, i.e. parallel to the direction of the static magnetic field, thereby contributing to opposition in the rapid change of magnetic fields in the imaging volume. Moreover, in the configurations shown in JP 2-87505 the grooves in the outer peripheral part of the pole face have an increased reluctance to the propagation of magnetic fields near the grooves over the reluctance in the ungrooved portions thereof. This increased reluctance path produces inhomogeneities in the magnetic fields near these grooves over the magnetic fields propagating through the ungrooved portions thereof.

SUMMARY OF THE INVENTION

The current invention is characterized by the use of thin sheets containing iron, preferably silicon iron sheet material as used in transformers layered as insulated disks on the surfaces of the pole pieces in close proximity of the gradient coils so that the sheets are formed as circular disks positioned substantially in rotational symmetry with the pole piece axis. The disks are formed and attached to their places by laminating using at least one or more plates and fixing these with glue, varnish or by mechanical means.

There are two types of design of the disks: in those parts where the disks are oriented along the plane of the pole piece face they consist of circular plates cut from iron sheet; in the parts oriented along the axis of the pole faces they consist of rings wound in the form of a spiral out of strip of iron sheet. In the case of circular plates the paths of eddy currents are broken by cutting narrow slots substantially perpendicular against the paths along which the gradient currents would have been set up; these slots are typically radially oriented. Moreover, the paths of eddy currents are further broken, while maintaining the homogeneity of the static magnetic field, by the plates being mounted in several insulated thin layers on top of each other preferably oriented with respect to each other such that their respective slots are not aligned.

One advantage of the invention is a decrease in eddy currents in the circumferential direction of each plate and/or parallel to the direction of the static magnetic field.

Mother advantage is improved homogeneity of the static magnetic field near the slots.

Still another advantage is easy implementation and no expensive materials are needed.

Still other advantages will become apparent to others upon reading and understanding the following Detailed Description.

DETAILED DESCRIPTION OF THE PREFERRED EMBODIMENT

Figure 1:
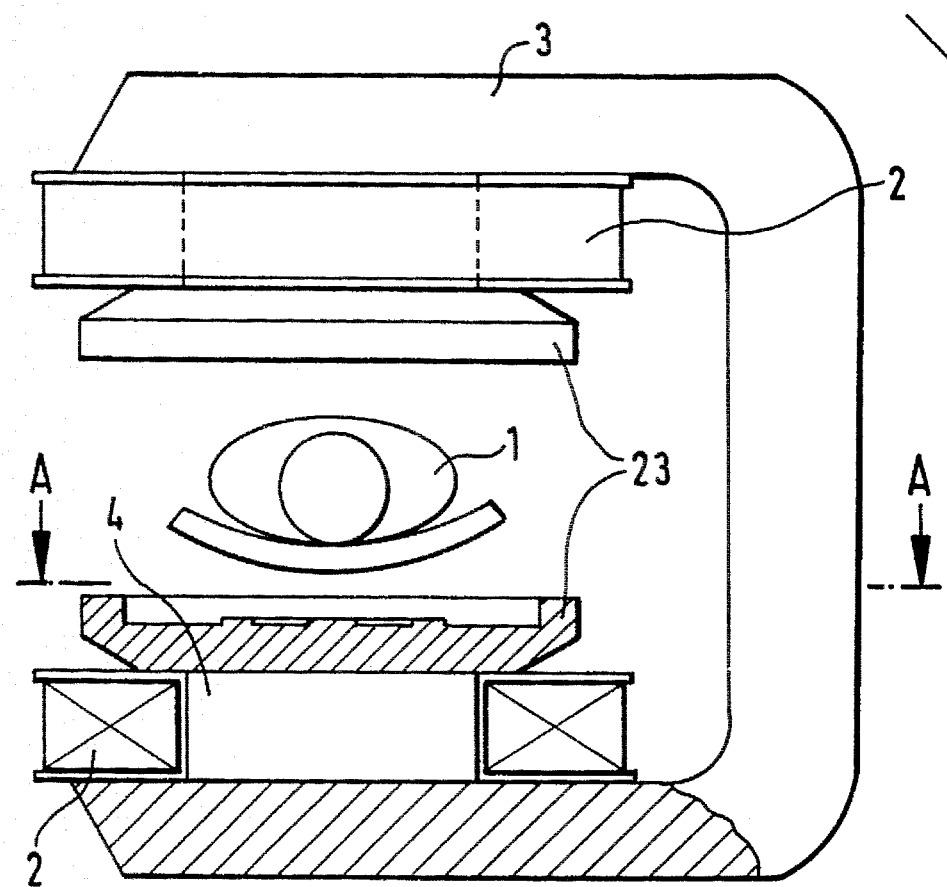
FIG. 1 shows the MRI equipment with pole pieces
Figure 1:
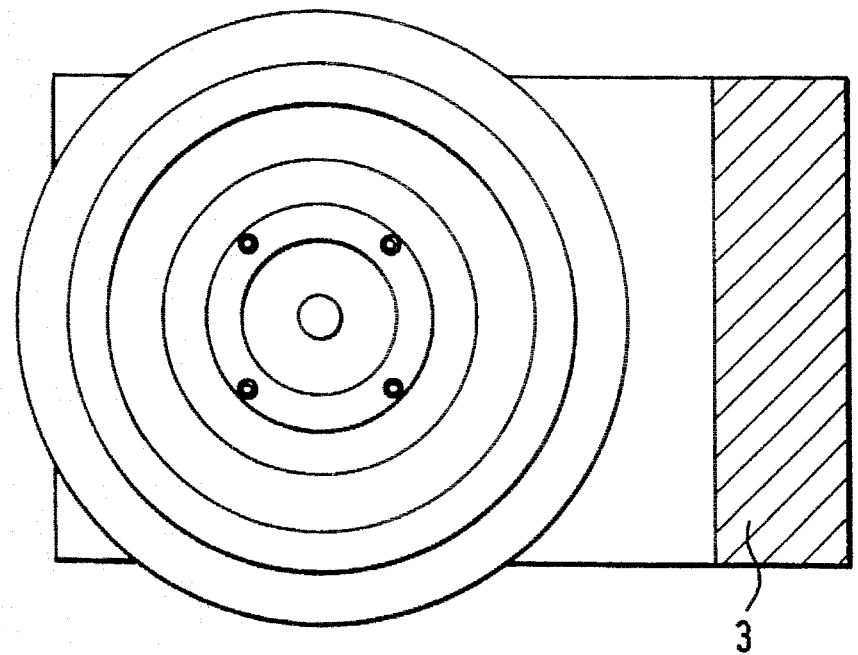

FIG. 1 shows the equipment for patient imaging, in which the patient 1 is lying between the pole pieces 23 in the magnetic field produced by current flowing in the coils 2. The necks 4 of the coils connect the pole pieces to the C-shaped body 3 of the magnet. These parts are made of iron and their function is to form the path for the return flux of the magnet. The invention is also perfectly usable for magnet designs based on permanent magnet material. These differ only in the sense that in between body 3 and pole pieces 23 instead of coils 2 and necks 4 permanent magnet material blocks are used.

Figure 2:
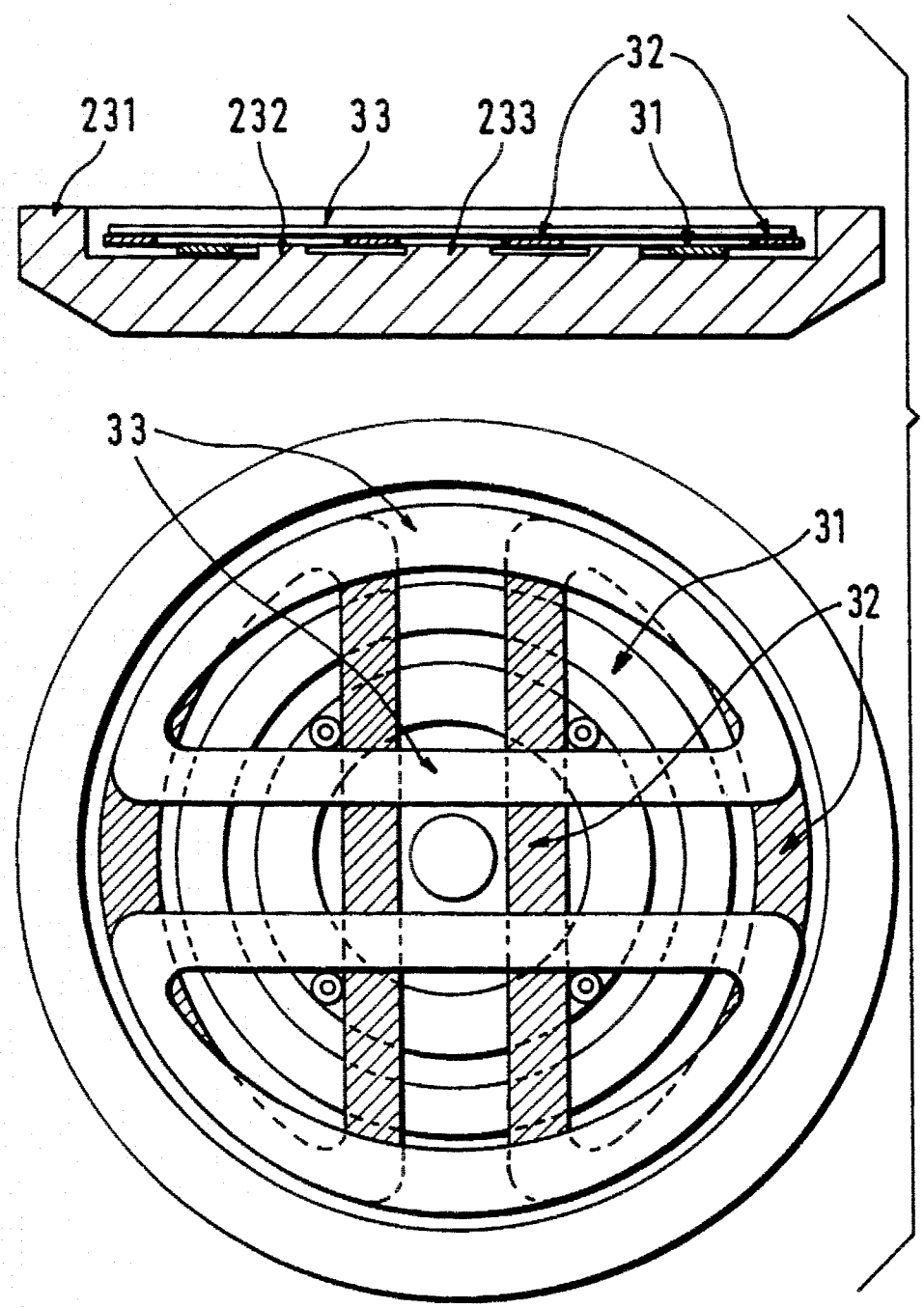
FIG. 2 shows the pole piece with gradient coils

FIG. 2 shows the cross section of the pole piece with gradient coils. In the drawing the Z-gradient coil 31 is placed closest to the pole piece, X-gradient coil pair 32 is in the next layer, and Y-gradient coil pair 33, perpendicular to the X-pair is placed in the outermost layer. The order is just an example, and gradients can be arranged in different orders. The coils typically consist of 10 turns of a conductor, and their forms shown here are simplified for clarity of the drawing. The pole pieces must include axially symmetrical rings, so called shim rings, in order to maximize the homogeneity of the static magnetic field. The largest one of these, the so called first shim 231, forms the outer rim. The next one 232 is typically roughly one half radius of the former and as an example the innermost 233 is a small ring at the center axis. Those skilled in the art know how to design these forms as well as how to design the forms of the gradient coils and this invention does not in any way alter the rules according to which these forms are computed.

Figure 3:
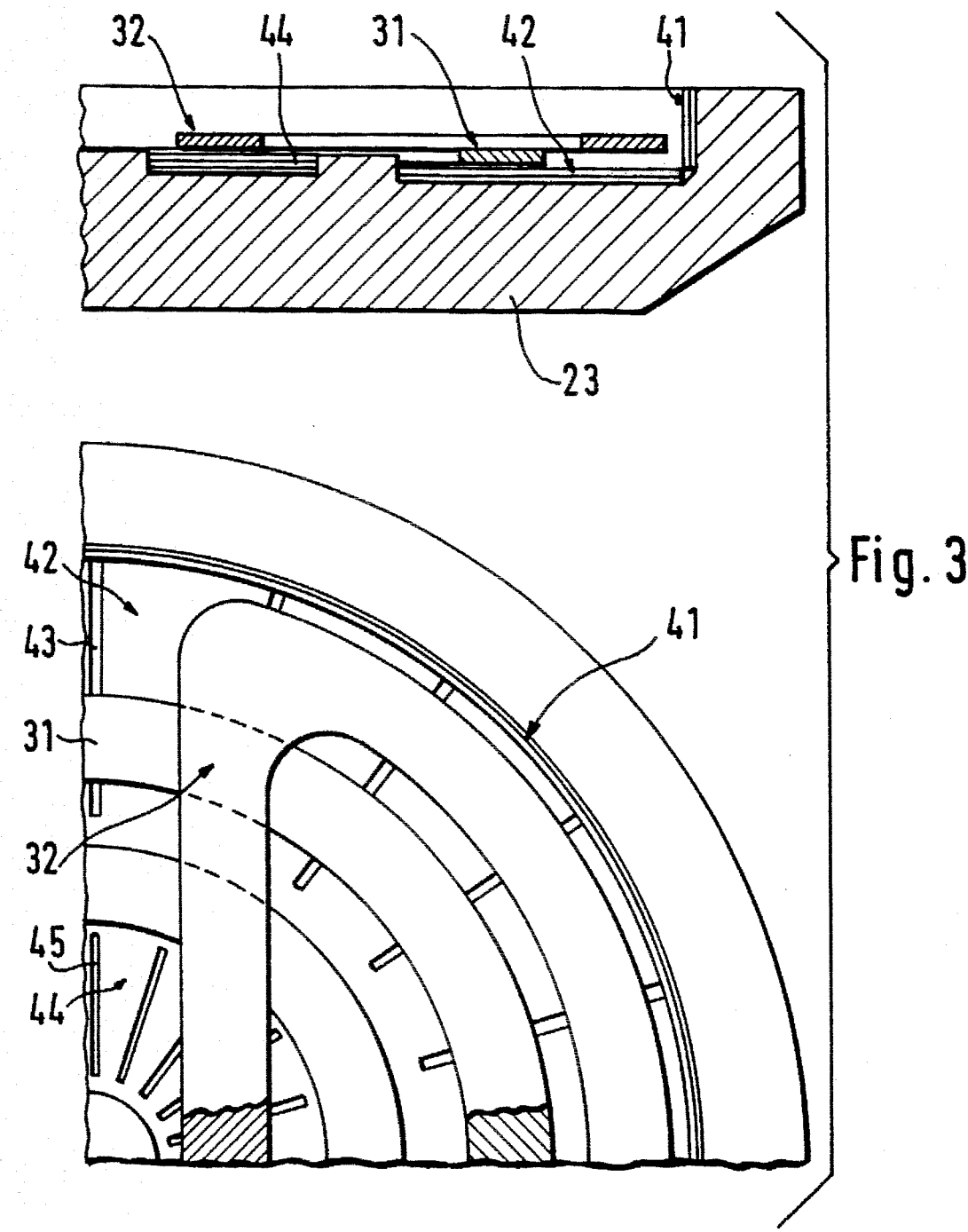
FIG. 3 shows one quarter of the pole piece

FIG. 3 shows one advantageous embodiment of the invention, but the invention is not restricted to just one certain combination of elements presented here. Here a quarter of the pole piece is shown with the thin sheets 44 and 42 and part 41 wound from iron strip. In the drawing are shown part of the Z-gradient coil with its cross section and part of the X-gradient coil 32 plus its cross section. Below these coils, grooves have been machined into the pole piece faces for the circular laminated sheets 42 and 44 and for the strip 41 wound into the shape of a ring. These grooves are dimensioned so that the sheets 42,44 and strip wound ring 41 snugly fit into the grooves keeping the overall dimensions and the mount of iron in the pole piece face, and thus also the homogeneity of the field, unchanged, as compared to a conventional design based on pole piece with corresponding dimensions. Moreover, one can cut slots 43 and 45 into the disks 42 and 44, the measurements of the slots are in no way critical. These slots increase the electrical resistance especially in the circumferential direction. The direction of the main magnetic flux is not significantly changed since, in the case of the plates consisting of several laminated layers, the position of the slots in different layers have been rotated with respect to each other.

Figure 4A:
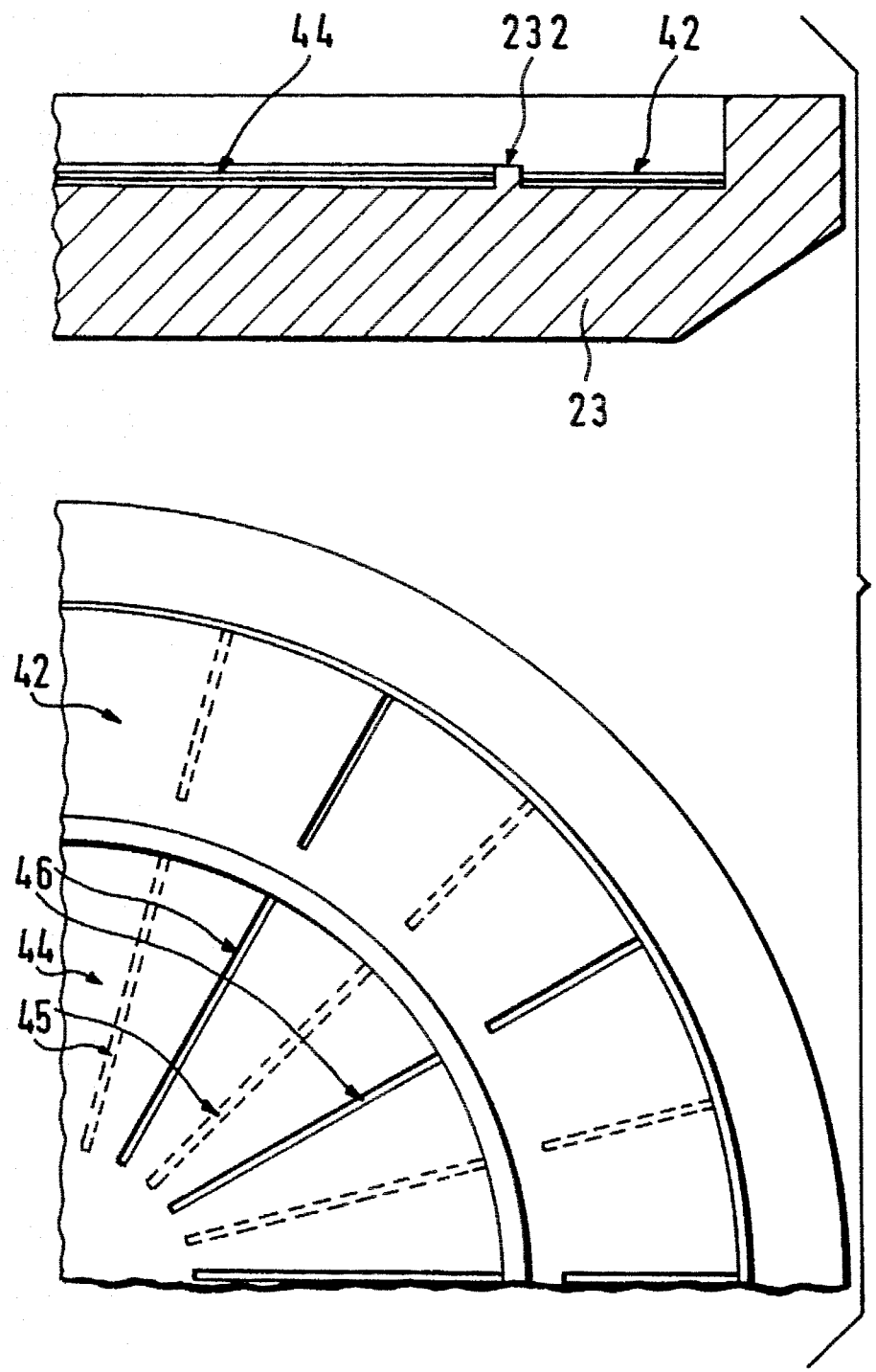
FIGS. 4A and 4B show details of the applications of the invention

FIG. 4A shows a simple embodiment of the invention when the pole piece is mostly of a flat shape. The gradient coils are not shown in order to increase the clarity. The disks 44 are mounted in the groove made into the shim ring 233 and between them and the outer ring, the disks 42 are mounted. Both disks are most conveniently fixed into place with glue. The disks are arranged so that the slots 46 are on different location as the slots 45 of the nearest disk. These slots 45 are drawn with dashed lines as they are behind the first plate. The same arrangement is true for disks 42. The amount of layers is for example conveniently four. This results when using half millimeter thick sheets, in a total thickness of two millimeters, which is a small portion of the total thickness of the pole piece of over 100 millimeters. Measurements made using the construction shown in FIG. 4A with four 0.5 mm FeSi-transformer plates show one order of magnitude increase in the gradient field ramping rate, when each plate has 18 radial slots with 20 degrees intervals. Increasing the amount of plates beyond four did not increase the ramp rate significantly.

Figure 4B:
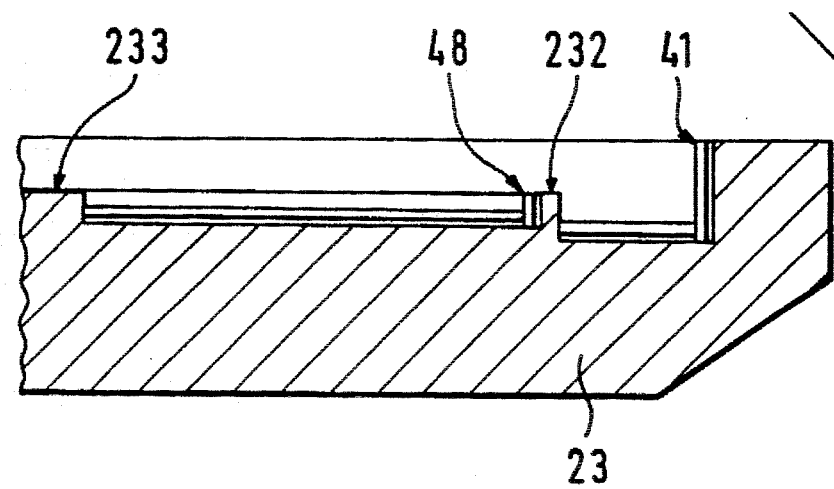
Figure 4B:
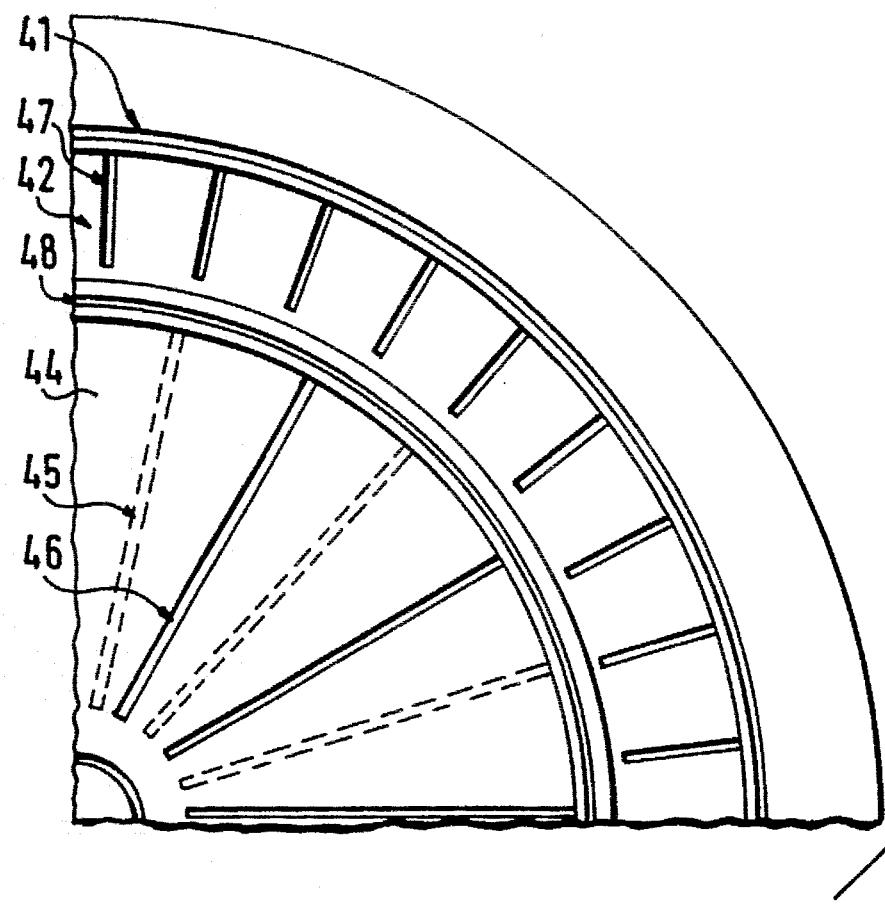

FIG. 4B shows a case with a more advanced pole piece form to further improve the homogeneity of the static magnetic field. In the middle of the pole piece there is innermost a shim 233, the second shim 232 being of considerable size has been covered with a strip 48 wound as a spiral made of some iron containing ferromagnetic material preferably of transformer sheet of 0.3–0.5 millimeter thickness. Inexpensive material with non oriented crystals can be used. On the inner surface of the outer rim similarly attached there are a few layers of strip of the same type to form ring 41. Inside of this ring there is a set 42 of thin disks, in which radial slots 47 are cut reaching neither the inner nor the outer perimeter of the disks, thus retaining the integrity and ease of handling these disks, but still increasing substantially the electrical resistance of this plate in its tangential direction. Also the structure wound into a spiral form diminishes the eddy currents as compared to the case when those areas in the iron pole piece are not covered.

The thickness of the iron plates can be in the range 0.2–5 mm, preferably in the range 0.3–1 mm, and radial slots can be cut into the plates to increase the electrical resistance in tangential direction. These plates are placed on top of each other in quantities ranging from one to ten, and they are electrically insulated from each other and rotated in such a way that the radial slots do not coincide. Thus the flux carrying capacity is kept high in all directions, and especially the gradient fluxes flow in the direction of the plane of these plates, which thus prevent the changing gradient fields from penetrating deeper into the bulk iron and thus causing disadvantageous eddy currents. In the surfaces in the direction of the rotational axis the structure is also substantially rotationally symmetric which is achieved by winding the sheet into a spiral form. The sheet is electrically insulated by glue or varnish so that the metal surfaces of the turns do not touch each other or the cavity walls. The design increases the gradient field strength due to the high permeability of the sheets almost to double the value observed in the free space. This is achieved without the eddy current problems encountered with conventional pole pieces. The explanation to the surprisingly good results is that the electrical resistance in the direction of eddy currents is raised by this invention to a value exceeding that of the bulk iron by orders of magnitude. Consequently the rise times of the gradient fields are reduced to less than one tenth.

An arrangement according to the invention at hand makes it possible and simple to design a pole piece of high permeability, resulting in a strong field, while at the same time eliminating the eddy currents and thus allowing the use of very fast gradients displaying rise times as short as 200 microseconds. Simultaneously the eddy current losses and the temperature rise in the pole pieces are remarkably low.

Figure 5:
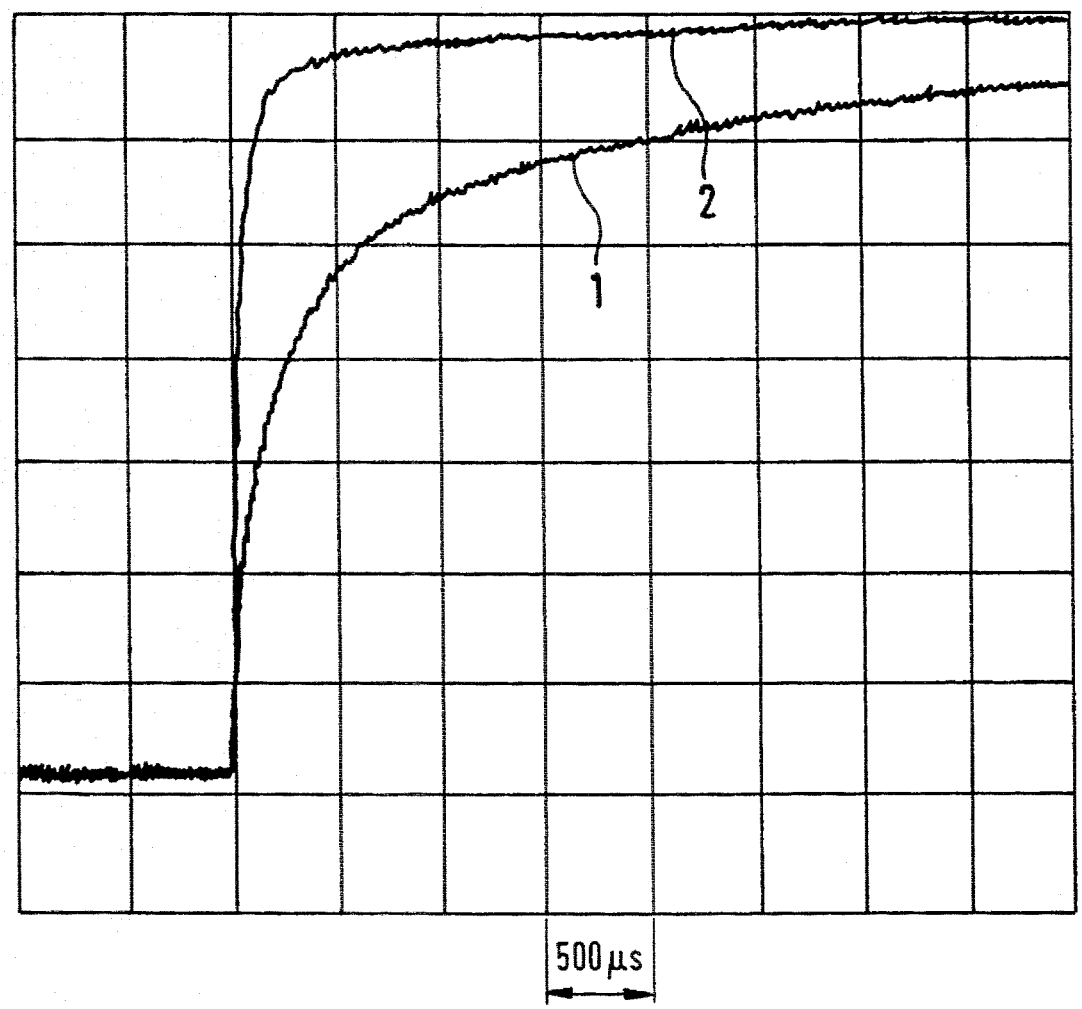
FIG. 5 shows the measured speeding up of the step response of the gradient field.

In FIG. 5 there is a comparison between the curve 1 of the rise of the gradient field when using a conventional pole piece while the measurement of the gradient field rise time when applying the invention in otherwise exactly similar circumstances resulted in curve 2. The time unit is 500 microseconds per division in the horizontal axis and the vertical axis presents the gradient field in the same arbitrary units in both cases. This result was achieved with four 0.5 mm thick circular transformer plates with radial slots with 20 degrees intervals, and the plates were glued to each other and to the pole piece.

I claim:

1. A magnetic resonance imaging system comprising:

a magnetically permeable core;

two pole pieces, each having a face, said pole pieces disposed on said core such that the pole piece faces are in opposed relationship forming a gap therebetween;

means for producing a main magnetic field in the gap;

a gradient coil disposed between the pole piece faces and adjacent one of the pole piece faces; and two or more circular sheets of electrically insulated ferromagnetic material disposed between the face of a pole piece and the gradient coil, said sheets laminated on top of each other into two or more layers in a direction substantially parallel to the face of the pole piece, each sheet having one or more slots therein and arranged in relationship to each other such that the slots of one layer do not align with the slots of the next layer, said sheets being axially symmetric to the face of the pole piece.

2. The magnetic resonance imaging system as set forth in claim 1 wherein each slot extends in a radial direction.

3. The magnetic resonance imaging system as set forth in claim 1 wherein the angular displacement between two or more adjacent slots of a sheet is preferably 15 to 30 degrees.

4. The magnetic resonance system as set forth in claim 1 wherein each slot extends substantially over the radius of its respective sheet.

5. The magnetic resonance imaging system as set forth in claim 1 wherein at least one of the circular sheets is comprised of silicon iron having a typical thickness in the range of 0.3–0.6 millimeters.

6. The magnetic resonance imaging system as set forth in claim 1 further including a spiral wound strip comprised of a thin and substantially insulated ferromagnetic strip disposed adjacent and substantially perpendicular to the face of the pole piece.

7. The magnetic resonance imaging system as set forth in claim 6 wherein the pole face includes an axially symmetrical shim ring extending generally into the gap and wherein said spiral wound strip is disposed on an inner part of said shim ring.

8. The magnetic resonance imaging system as set forth in claim 6 wherein the ring shaped layer is formed by concentrically winding a thin and substantially insulated ferromagnetic strip.

9. The magnetic resonance imaging system as set forth in claim 7 wherein the shim ring is disposed at the outer edge of the pole piece and wherein at least the inner part of the shim ring is perpendicular to the pole face such that the spiral wound strip disposed on said shim ring is perpendicular to the pole face.

10. The magnetic resonance imaging system as set forth in claim 6 wherein the spiral wound strip is comprised of silicon iron having a typical thickness in the range of 0.3–0.6 millimeters.

11. The magnetic resonance imaging systems of claim 1 wherein each of the pole pieces includes at least one axially symmetric shim ring.

12. The magnetic resonance imaging system of claim 11 further comprising a spiral wound strip of ferromagnetic material disposed adjacent to a shim ring and substantially perpendicular to the face of the pole piece.

13. The magnetic resonance imaging system of claim 1 wherein each of the pole pieces further comprise one or more circular grooves to receive the laminated circular sheets.

14. The magnetic resonance imaging system of claim 1 wherein each layer is comprised of a single sheet.

15. A magnetic field generating device for use in magnetic resonance apparatus comprising:

a pair of pole pieces disposed to face each other with a gap formed therebetween;

a magnetically permeable core for coupling the pole pieces;

means for producing a magnetic field in the gap;

a plurality of sheets of insulated ferromagnetic material disposed adjacent the face of a pole piece, each sheet including one or more radially extending slots, said sheets laminated on top of each other into two or more layers and arranged in relationship such that the slots of one layer do not coincide with the slots of another layer, said sheets being axially symmetric to the face of the pole piece.

16. A magnetic field generating device for use in magnetic resonance apparatus comprising:

a pair of pole pieces disposed to face each other with a gap formed therebetween;

a magnetically permeable core for coupling the pole pieces;

means for producing a magnetic field in the gap;

a first circular shaped sheet of insulated ferromagnetic material disposed adjacent and axially symmetric to the face of a pole piece, said first sheet having an outside diameter less than the diameter of the pole face and one or more radially extending slots therein;

a second circular shaped sheet of insulated ferromagnetic material disposed adjacent and axially symmetric to the face of the pole piece, said second sheet having an inside diameter greater than the outside diameter of the first sheet and having one or more radially extending slots therein.

17. The magnetic field generating device of claim 16 further comprising an axially symmetric shim ring extending generally into the gap and separating the second circular sheet from the first circular sheet.

\* \* \* \* \*